United States Patent
Fischer et al.

(10) Patent No.: US 7,070,757 B2
(45) Date of Patent: Jul. 4, 2006

(54) METHOD FOR PRODUCING CATALYSTS CONSISTING OF METAL OF THE PLATINUM GROUP BY MEANS OF ELECTROLESS DEPOSITION AND THE USE THEREOF FOR THE DIRECT SYNTHESIS OF HYDROGEN PEROXIDE

(75) Inventors: Martin Fischer, Ludwigshafen (DE); Thomas Butz, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 107 days.

(21) Appl. No.: 10/381,594

(22) PCT Filed: Oct. 1, 2001

(86) PCT No.: PCT/EP01/11347

§ 371 (c)(1),
(2), (4) Date: Apr. 2, 2003

(87) PCT Pub. No.: WO02/28527

PCT Pub. Date: Apr. 11, 2002

(65) Prior Publication Data

US 2004/0037770 A1    Feb. 26, 2004

(30) Foreign Application Priority Data

Oct. 2, 2000   (DE) ................. 100 48 844

(51) Int. Cl.
  *C01B 15/29*   (2006.01)
  *C07C 5/03*    (2006.01)
  *C07C 5/05*    (2006.01)
  *C07C 5/08*    (2006.01)
  *C07C 5/09*    (2006.01)

(52) U.S. Cl. ............... 423/584; 423/659; 502/325; 502/339; 585/273; 585/275

(58) Field of Classification Search ............... 423/584, 423/588, 403, 659; 502/325, 339; 585/273, 585/275
See application file for complete search history.

(56) References Cited

U.S. PATENT DOCUMENTS

| | | | |
|---|---|---|---|
| 3,696,939 A | 10/1972 | Leaman | |
| 4,189,405 A * | 2/1980 | Knapton et al. | 502/73 |
| 4,341,662 A * | 7/1982 | Pfefferle | 502/201 |
| 4,471,014 A | 9/1984 | den Hartog et al. | |
| 4,731,229 A | 3/1988 | Sperandio | |
| 4,869,891 A * | 9/1989 | Handley | 423/403 |
| 5,082,647 A | 1/1992 | Chuang | |
| 5,338,531 A | 8/1994 | Chuang et al. | |
| 5,690,900 A * | 11/1997 | Smojver | 423/392 |
| 5,985,235 A * | 11/1999 | Nystrom et al. | 423/588 |
| 6,207,128 B1 * | 3/2001 | Sellin et al. | 423/588 |
| 6,297,185 B1 * | 10/2001 | Thompson et al. | 502/101 |
| 6,325,910 B1 | 12/2001 | Meyer et al. | |
| 6,375,920 B1 | 4/2002 | Fischer et al. | |
| 6,387,346 B1 * | 5/2002 | Bertsch-Frank et al. | 423/584 |
| 6,468,496 B1 * | 10/2002 | Jones et al. | 423/584 |
| 6,534,029 B1 * | 3/2003 | Klein et al. | 423/392 |
| 6,676,919 B1 * | 1/2004 | Fischer et al. | 423/584 |
| 2001/0036432 A1 * | 11/2001 | Hu et al. | 423/213.5 |
| 2002/0083643 A1 * | 7/2002 | Amendola et al. | 48/61 |
| 2003/0022788 A1 * | 1/2003 | Tanaka et al. | 502/325 |

FOREIGN PATENT DOCUMENTS

| | | |
|---|---|---|
| DE | 11 12 814 | 8/1961 |
| DE | 19 43 213 | 5/1971 |
| DE | 26 07 988 | 8/1977 |
| EP | 0 448 884 | 10/1991 |
| EP | 0 878 235 | 11/1998 |
| WO | 99 32398 | 7/1999 |

OTHER PUBLICATIONS

John R. Kosak: "A novel fixed bed catalyst for the direct combination of H2 and O2 to H2O2" Chem. Ind. (DECKER), vol. 62, Catalysis of Organic Reactions, pp. 115-123 1995, (no month).

European Office Action fo European Patent Appl. No. 01 969 806.7 dated Feb. 3, 2005.

* cited by examiner

*Primary Examiner*—Wayne A. Langel
(74) *Attorney, Agent, or Firm*—Oblon, Spivak, McClelland, Maier & Neustadt, P.C.

(57) ABSTRACT

Catalysts produced by electroless deposition of at least one platinum metal on a nonporous nonmetallic support can be used for the synthesis of hydrogen peroxide from the elements and for the hydrogenation of organic compounds.

23 Claims, No Drawings

METHOD FOR PRODUCING CATALYSTS CONSISTING OF METAL OF THE PLATINUM GROUP BY MEANS OF ELECTROLESS DEPOSITION AND THE USE THEREOF FOR THE DIRECT SYNTHESIS OF HYDROGEN PEROXIDE

The present invention relates to a process for producing catalysts by electroless deposition of at least one platinum metal on a nonporous nonmetallic support, to the catalysts obtainable by this process, to the use of the catalysts for the synthesis of hydrogen peroxide from the elements and for the hydrogenation of inorganic and organic compounds and to a process for preparing hydrogen peroxide and a process for catalytic reduction using these catalysts.

Catalysts comprising platinum metals as catalytically active substances are used in many forms and have great industrial importance, e.g. in the reduction or hydrogenation of organic compounds and in the catalytic purification of waste gases from industry and motor vehicles.

For industrial applications, use is made where possible of supported platinum metal catalysts which have only small amounts of the expensive noble metals on usually catalytically inactive support materials having a large surface area, e.g. carbon, aluminum oxide, silicon oxide, ceramic or other mineral supports. The application of the catalytically active metals to such porous supports is usually carried out by impregnation of the supports with solutions of salts or organometallic compounds of the catalytically active metal and subsequent immobilization by precipitation, hydrolysis, heat treatment, calcination and/or activation.

EP-A-0 875 235 describes a process for producing supported noble metal catalysts on porous oxidic supports by electroless deposition of noble metals from aqueous solutions using reducing agents and in the presence of complexing agents.

DE-A-44 12 463 describes the use of a colloidal palladium solution comprising at least one reducing agent and at least one protective colloid and also at least one noble metal or noble metal compound for the pretreatment of electrically nonconductive substrate surfaces before they are metallized by means of a metallizing solution. The deposition of at least one platinum metal on a nonporous nonmetallic support is not described. Furthermore, this document provides no teachings regarding the production of catalysts.

U.S. Pat. No. 5,082,647 describes a process for the direct synthesis of hydrogen peroxide which uses a catalyst comprising at least one metal of transition group VIII on a hydrophobic support. Hydrophobic support materials used are, inter alia, styrene-divinylbenzene copolymers, homopolymers and copolymers of ethylene and propylene, hydrophobicized silicon dioxide, polytetrafluoroethylene, fluorinated carbon and carbon which has been hydrophobicized by treatment with a silane or with fluorene. The hydrophobic support has a surface area of at least 50 m²/g.

WO-A-99/32398 describes a process for the direct synthesis of hydrogen peroxide, in which catalysts on supports having low BET surface areas of preferably less than 1 m² per ml of reactor volume are said to be used. Support materials proposed are nonporous nonmetals such as glass, quartz and organic polymers. As regards the production of the catalysts, reference is simply made to the disclosure of EP-A-0 878 235, U.S. Pat. No. 5,338,531 and J. R. Kosak "A new novel fixed bed catalyst for the direct combination of $H_2$ and $O_2$ to $H_2O_2$", Chem. Ind. (Dekker), 1995, Volume 62, Catalysis of Organic Reactions. However, none of the references cited describes the production of catalysts on non-metallic pore-free supports. According to the working example of WO-A-99/32398, a catalyst is produced by impregnating unpretreated glass wool with palladium chloride and hexachloroplatinic acid and subsequently reducing the metals by means of hydrogen at 300° C. In the subsequent preparation of hydrogen peroxide using this catalyst in the gas phase, only extremely low space-time yields of about 5 g/l×h are achieved.

It is an object of the present invention to provide a process for producing improved nonmetal-supported platinum metal catalysts. Essentially complete deposition of the expensive platinum metal and/or good adhesion of the noble metal to the nonmetallic support should preferably be ensured in this process. Furthermore, the catalysts should have a high catalytic activity and selectivity in hydrogenations, particularly in the direct synthesis of $H_2O_2$ from hydrogen and oxygen. The catalysts should preferably have improved operating lives.

We have found that this object is achieved by a process for producing catalysts comprising at least one platinum metal on a nonporous nonmetallic support, which comprises firstly activating the support and then electrolessly depositing at least one platinum metal on the support which has been pretreated in this way. For the electroless deposition, an aqueous medium comprising at least one compound or one complex of a platinum metal and at least one reducing agent is brought into contact with the support. In contrast to the catalysts known from the prior art, the catalysts produced according to the present invention have excellent catalyst properties. In addition, essentially quantitative deposition of the platinum metal from the solution can be achieved. Surprisingly, good adhesion of the platinum metals to the nonporous nonmetallic supports used is also achieved. Thus, the catalytic coatings produced according to the present invention have a high abrasion resistance even under severe mechanical stress, as occurs, for example, in the synthesis of hydrogen peroxide. In general, no mechanical detachment is observed even after prolonged operation.

The present invention provides a process for producing a catalyst comprising at least one platinum metal on a nonporous nonmetallic support, which comprises
a) if desired, roughening the surface of the support,
b) activating the support, which may have been roughened on the surface, by treating it, preferably with a reducing agent and a salt of a platinum metal,
c) electrolessly depositing at least one platinum metal on the support which has been treated as described in step b), by bringing an aqueous medium comprising at least one compound or one complex of a platinum metal and at least one reducing agent into contact with the support, and
d) if desired, activating the catalyst obtained in step c).

According to the present invention, a nonporous support is used for producing the catalyst. For the purposes of the present invention, a nonporous support is a support having a mercury (Hg) porosymmetry pore volume of not more than 1.0 ml/g, preferably not more than 0.1 ml/g and more preferably not more than 0.05 ml/g. The ratio of pore volume to total volume of the support workpiece is preferably not more than 2%, more preferably not more than 0.5%.

The supports used according to the present invention preferably have a BET surface area of not more than 5 m²/g, in particular not more than 0.2 m²/g.

The nonmetallic material used as support is preferably selected from among mineral materials, plastics and mixtures and combinations thereof.

For the purposes of the present invention, the expression "mineral material" encompasses quite generally nonmetallic inorganic materials such as natural and synthetic minerals, glasses, ceramics, etc. Preference is given to using a glass as mineral material. Preference is given to glasses made of fused silicon dioxide or fused quartz and glasses based on alkali metal silicates, alkaline earth metal silicates, borosilicate, aluminosilicate and lead silicate. Further preferred mineral support materials are borate, phosphate, germanate, chalcogenide and halide glasses, e.g. glass made of beryllium fluoride.

Mineral materials selected from among ceramic materials are also preferred as supports. Suitable ceramic materials can be produced from metal oxides, borides, nitrides and/or carbides. The ceramic materials used according to the present invention can be glazed or unglazed, crystalline or partially crystalline. In the process of the present invention, preference is given to using ceramics based on aluminum oxide, silicon carbide, silicon nitride, zirconium dioxide or a mixture thereof. Further preferred ceramics are ones containing cations, for example chelatite, steatite, cordierite, anorthite, mullite or pollucite. Ceramic composite materials are also preferred.

According to a further preferred embodiment, a plastic support is used in the process of the present invention.

The supports used according to the present invention preferably comprise at least one natural or synthetic polymeric material.

Examples of such materials are:

1. Polymers of monoolefins and diolefins, for example polypropylene, polyisobutylene, poly-1-butene, poly-4-methyl-1-pentene, polyisoprene or polybutadiene, and also polymers of cycloolefins such as cyclopentene or norbornene; also polyethylene (which may be crosslinked or uncrosslinked), e.g. high density polyethylene (HDPE), high density polyethylene having a high molecular weight (HDPE-HMW), high density polyethylene having an ultra-high molecular weight (HDPE-UHMW), medium density polyethylene (MDPE), low density polyethylene (LDPE), linear low density polyethylene (LLDPE), branched low density polyethylene (HP-LDPE).

2. Mixtures of polymers listed under 1., e.g. mixtures of polypropylene with polyisobutylene, polypropylene with polyethylene (e.g. PP/HDPE, PP/LDPE) and mixtures of various types of polyethylene (e.g. LDPE/HDPE).

3. Copolymers of monoolefins and diolefins with one another or with other vinyl monomers, e.g. ethylene-propylene copolymers, and mixtures thereof with other polymers, e.g. polyamides.

4. Polyvinylaromatics, e.g. polystyrene, poly(p-methylstyrene), poly(α-methylstyrene).

5. Copolymers of polyvinylaromatics such as styrene or α-methylstyrene with dienes or acrylic derivatives, e.g. styrene-butadiene, styrene-acrylonitrile, styrene-alkyl methacrylate, styrene-butadiene-alkyl acrylate and methacrylate, styrene-maleic anhydride, styrene-acrylonitrile-methyl acrylate; high-impact mixtures of styrene copolymers and another polymer, e.g. a polyacrylate, a diene polymer or an ethylene-propylene-diene terpolymer; and also block copolymers of styrene, e.g. styrene-butadiene-styrene, styrene-isoprene-styrene, styrene-ethylene/butylene-styrene or styrene-ethylene/propylene-styrene.

6. Graft copolymers of vinylaromatics such as styrene or α-methylstyrene, e.g. styrene on polybutadiene, styrene on polybutadiene-styrene or polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene-propylene-diene terpolymers, styrene and acrylonitrile on polyalkyl acrylates or polyalkyl methacrylates, styrene and acrylonitrile on acrylate-butadiene copolymers, and also their mixtures with copolymers mentioned under 5., as are known, for example, as ABS, MBS, ASA or AES polymers.

7. Halogen-containing polymers such as polychloroprene, chlorinated rubber, chlorinated and brominated copolymer of isobutylene-isoprene (halobutyl rubber), chlorinated or chlorosulfonated polyethylene, copolymers of ethylene and chlorinated ethylene, epichlorohydrine homopolymers and copolymers, in particular polymers of halogen-containing vinyl compounds, e.g. polyvinyl chloride, polyvinylidene chloride, polyvinyl fluoride, polyvinylidene fluoride; and also their copolymers such as vinyl chloride-vinylidene chloride, vinyl chloride-vinyl acetate or vinylidene chloride-vinyl acetate.

8. Polymers derived from α,β-unsaturated acids and their derivatives, e.g. polyacrylates and polymethacrylates, polymethyl methacrylates which have been impact-modified using butyl acrylate, polyacrylamides and polyacrylonitriles.

9. Copolymers of the monomers mentioned under 8. with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers.

10. Polyurethanes.

11. Polyamides and copolyamides derived from diamines and dicarboxylic acids and/or from aminocarboxylic acids or the corresponding lactams, e.g. polyamide 4, polyamide 6, polyamide 6/6, 6/10, 6/9, 6/12, 4/6, 12/12, polyamide 11, polyamide 12, aromatic polyamides, e.g. derived from p-phenylenediamine and adipic acid; polyamide prepared from hexamethylenediamine and isophthalic and/or terephthalic acid and, if desired, an elastomer as modifier, e.g. poly-2,4,4-trimethylhexamethyleneterephthalamide or poly-m-phenyleneisophthalamide. Also suitable are block copolymers of the abovementioned polyamides with polyolefins, olefin copolymers, ionomers or chemically bound or grafted elastomers; or with polyethers such as polyethylene glycol, polypropylene glycol or polytetramethylene glycol. Further suitable polyamides are polyamides or copolyamides modified with EPDM or ABS; and also polyamides condensed during processing ("RIM polyamide systems").

12. Polyureas, polyimides, polyamidimides, polyetherimides, polyesterimides, polyhydantoins and polybenzimidazoles.

13. Polyester derived from dicarboxylic acids and dialcohols and/or from hydroxycarboxylic acids or the corresponding lactones, e.g. polyethylene terephthalate, polybutylene terephthalate, poly-1,4-dimethylolcyclohexane terephthalate, polyhydroxybenzoates, and also block polyether esters derived from polyethers having terminal hydroxyl groups; also polyesters modified with polycarbonates or MBS.

14. Polycarbonates and polyester carbonates.

15. Crosslinked polymers derived, for example, from aldehydes and phenols, urea or melamine, e.g. phenol-formaldehyde, urea-formaldehyde and melamine-formaldehyde resins.

16. Crosslinkable acrylic resins derived from substituted acrylic esters, e.g. from epoxyacrylates, urethane acrylates or polyester acrylates.

17. Alkyd resins, polyester resins and acrylate resins crosslinked by means of melamine resins, urea resins, isocyanates, isocyanurates, polyisocyanates or epoxy resins.

18. Crosslinked epoxy resins derived from aliphatic, cycloaliphatic, heterocyclic or aromatic glycidyl compounds, e.g. products of bisphenol A diglycidyl ethers, bisphenol F diglycidyl ethers which have been crosslinked by means of customary hardeners, e.g. anhydrides or amines, with or without accelerators.

The support is preferably used in the form of a particulate, linear, sheet-like or three-dimensional structure. The term "particulate structures" encompasses the range from fine pigments through to macroscopic particles. It includes, in particular, particulate materials having a particle size of from 0.25 nm to 10 mm. Linear structures are, in particular, fibers, filaments and the like. The nonmetallic supports are preferably used in the form of glass or polymer fibers. Sheet-like structures are, in particular, woven fabrics, knitted fabrics, felts, nonwovens, meshes, mats, etc. Three-dimensional structures are shaped bodies in general of various dimensions.

The nonmetallic supports are preferably used in the form of shaped bodies. The shaped bodies can have the shape of spheres, pellets, short extrudates, Raschig rings, Pall® rings, saddles, cylindrical mesh packing elements, hackettes, spirals or helices.

The nonmetallic supports are also preferably used in the form of woven fabrics. The fabric can in turn be used in the form of monoliths, i.e. ordered packings.

Particularly suitable monoliths are made up of a plurality of layers of corrugated, creased and/or smooth woven fabrics which are preferably arranged so that adjacent layers form more or less closed channels. The hydraulic diameter of the channels is preferably in the range from 1 to 10 mm, in particular from 1.5 to 3 mm (in accordance with the definition in VDI-Wärmeatlas, Section LE 1). The channels can be straight or curved. Preference is given to using multilayer woven fabrics forming smooth and corrugated or creased channels. While shaped bodies are generally placed in the reactor as a loose bed, monoliths are preferably installed in the reactor, particularly in such a way that the channels are inclined to the flow direction of the reaction medium. The woven fabric layers themselves are preferably installed parallel to the flow direction in the reactor. If a plurality of these units are installed in series, they are preferably installed so that the flow channels are inclined alternately in different directions relative to the flow direction. The units are preferably installed so that the woven fabric layers of two successive units form an angle of preferably about 90° to one another. Rolled modules of corrugated or creased and, if desired, also flat layers of woven fabric are likewise suitable.

Step a)

In general, the nonporous nonmetallic supports used according to the present invention can be used for producing the catalyst in which they are obtained in their respective production process. However, if desired, the surface of the support can also be roughened prior to the subsequent process steps.

To roughen the support surface, it is possible to use mechanical and/or chemical methods. Roughening of supports made of mineral materials, e.g. vitreous or ceramic supports, is preferably carried out by known mechanical methods, e.g. by grinding using a material which has a hardness greater than that of the support. Suitable abrasives are, for example, quartz, corundum, garnet, emery and diamond. A suitable method of roughening glass or ceramic spheres is treatment with a finely pulverulent abrasive in a rotating drum. The abrasive can subsequently be separated from the support material by customary methods such as screening or rinsing with water. Vitreous surfaces can also be roughened by sand blasting.

A further suitable method of increasing the roughness of the support material is treatment with suitable chemicals. Mineral materials can advantageously be roughened on the surface by etching, e.g. with hydrofluoric acid, aqueous alkali or an aqueous mineral acid, e.g. hydrochloric acid, nitric acid, phosphoric acid. Supports made of plastic can advantageously be roughened by treatment with chemicals which attack the surface, preferably oxidizing agents. Suitable chemicals for roughening surfaces of plastics are, for example, nitric acid, hydrogen peroxide, ammonia, etc. Preference is given to using about 10% strength nitric acid, about 50% strength hydrogen peroxide or a mixture of about 10% strength ammonia and about 10% strength hydrogen peroxide, if appropriate for a number of hours and at elevated temperatures.

Step b)

By "activation" of the support is meant an operation in which nuclei for electroless deposition are formed on the surface. The nuclei for electroless deposition are generally metal, preferably a platinum metal and more preferably palladium. The support is preferably activated by treating it with a reducing agent and a salt of a platinum metal.

Treatment of the support with the reducing agent and with the platinum metal salt can be carried out simultaneously or in succession. In both cases, the treatment can be carried out in one or more steps. If desired, the support can be subjected to cleaning before the treatment. Likewise, a cleaning step can follow the treatment or, in the case of treatment in a plurality of steps, each treatment step.

In a first preferred embodiment, the treatment of the support in step b) is carried out using an aqueous medium comprising at least one reducing agent and at least one salt of a platinum metal. The treatment can be carried out in one or more steps.

In a further preferred embodiment, the treatment of the support in step b) is carried out separately using at least one reducing agent and at least one platinum metal salt. A preferred method of treating the support in step b) comprises the following substeps:

b1) if appropriate, cleaning the support,
b2) treating the support with an aqueous medium comprising at least one reducing agent,
b3) treating the support with an aqueous medium comprising at least one salt of a platinum metal, where the steps b2) and b3) can be carried out one or more times. The treatment can be commenced and concluded either with step b2) or with step b3). The steps b2) and b3) are preferably carried out from one to ten times.

If desired, the treatment steps b2) and/or b3) can be followed by a cleaning step, e.g. by bringing the support into contact with a rinsing solution.

The cleaning of the support prior to the treatment steps can be carried out by customary methods known to those skilled in the art. These include, for example, treatment with aqueous surfactant solutions, and/or treatment with organic solvents and solvent mixtures, e.g. ethanol, ethanol/water mixtures, ethyl acetate, acetone, etc. If desired, cleaning can be carried out under the action of ultrasound. Suitable rinsing solutions for cleaning the support after a treatment step are, for example, the pure aqueous media used for the treatment steps and, in particular, water.

Suitable aqueous media for the treatment steps are mentioned below for step c), which is incorporated by reference at this point. Step b) is preferably carried out using an aqueous medium which is essentially free of organic solvents. This medium preferably further comprises at least one inorganic acid, in particular hydrochloric acid. The aqueous media used in step b) preferably have an acidic pH. Particular preference is given to a pH of $\leq 6$, in particular $\leq 5$.

For treatment of the support with the reducing agent (and if desired simultaneously with the platinum metal salt), use is made of an aqueous medium comprising at least one reducing agent in fully or partly dissolved form. Suitable reducing agents are mentioned below for step c), which is incorporated by reference at this point. Reducing agents which are preferred for use in step b) are tin(II) chloride and titanium(III) chloride.

Platinum metal salts which are suitable for treatment of the support in step b) are mentioned under step c) below, which is incorporated by reference at this point. Preference is given to using at least one palladium salt as platinum metal salt. The aqueous medium used for treatment of the support in step b) can further comprise, in addition to at least one platinum metal salt, at least one further salt of a metal of the iron group and/or transition group 1. Preference is given to nickel salts and silver salts.

In a preferred embodiment, the treatment of the support in step b) is carried out by bringing it into contact with an aqueous medium having a tin(II) chloride content in the range from about 1 to 20 g/l and a content of concentrated hydrochloric acid of from about 1 to 50 ml/l. The treatment is preferably carried out at from about 10 to 40° C., in particular at ambient temperature. The duration of the treatment with the reducing agent is preferably in a range from about 0.1 to 30 minutes, in particular from 0.5 to 10 minutes. The support is preferably rinsed with water after treatment with the reducing agent. It is subsequently brought into contact with an aqueous medium having a palladium chloride content in the range from about 0.02 to 2 g/l and a content of concentrated hydrochloric acid in the range from about 0.1 to 10 ml/l. This aqueous medium can further comprise other metal salts, as described above. The treatment with the platinum metal is likewise preferably carried out at from about 10 to 40° C., in particular at ambient temperature. The treatment time is preferably in a range from about 0.1 to 30 minutes, particularly preferably from 0.5 to 10 minutes. The treated support is then preferably rinsed again with water.

In a further preferred embodiment, an aqueous medium comprising at least one platinum metal salt and, if desired, at least one further salt of a metal of the iron group or of transition group 1 is firstly provided for the treatment of the support in step b) and the support is subsequently brought into contact therewith. The support is preferably treated with the solution provided for a period of about 24 hours. The treated support is then preferably rinsed with water.

The amount of platinum metal deposited on the support in step b) is small compared to the total amount deposited on the support. The amount of platinum metal deposited in step b) is preferably not more than 10% by weight, particularly preferably not more than 1% by weight, of the total amount deposited on the support.

The pretreatment of the support in step b) of the process of the present invention assists in producing catalysts in which the platinum metal adheres well to the nonporous support material. The catalytic coatings produced in this way display a high abrasion resistance even in the case of severe mechanical stress.

If desired, the support which has been pretreated in this way can subsequently be dried by customary methods known to those skilled in the art. However, it can also be used moist for the subsequent treatment in step c).

Step c)

For the purposes of the present invention, platinum metals are the metals of transition group 8 of the Periodic Table other than those of the iron group, namely ruthenium, rhodium, iridium, palladium, osmium and platinum. Preference is given to ruthenium, rhodium, palladium and platinum, particularly preferably palladium and platinum. The catalysts of the present invention can comprise a plurality of platinum metals. All combinations of the abovementioned platinum metals are suitable; preference is given to combinations of palladium and platinum, of palladium and rhodium, of palladium and iridium, of palladium, platinum and rhodium and of palladium, platinum and iridium. A particularly preferred combination is palladium and platinum. In the combinations which include palladium, palladium is preferably the main platinum metal component. The proportion of palladium is then preferably above 40% by weight, preferably above 60% by weight and particularly preferably above 80% by weight, based on the total platinum metal content. The further platinum metals which may be present as secondary constituents can each make up upto 30% by weight, preferably upto 20% by weight and particularly preferably upto 15% by weight, of the total platinum metal content. The platinum metals preferably comprise from 80 to 100% by weight of palladium and from 0 to 20% by weight of platinum or iridium. In most cases, from 1 to 3 of the abovementioned platinum metals make up more than 95% by weight of the total amount of platinum metals used. if further platinum metals are present in addition to a main platinum metal, these are generally present in amounts of greater than 0.001% by weight, preferably greater than 0.01% by weight, e.g. in amounts of about 0.1% by weight, about 1% by weight or about 5% by weight.

The catalytically active component of the catalysts of the present invention may further comprise, apart from platinum metals, other elements as additive components or possibly in the form of impurities. Preferred additive components which, for example, can influence the activity and/or selectivity of the catalysts are selected from among metals, nonmetals and their compounds. These preferably include metals such as cobalt, nickel, copper, silver, gold, chromium, molybdenum, tungsten, manganese, rhenium, aluminum, tin, lead, arsenic, antimony and bismuth, and nonmetals such as boron, carbon, silicon, nitrogen and phosphorus. The metals and nonmetals mentioned can be present both in ionic form and in nonionic form in the catalytically active coating. Furthermore, the catalytically active component can further comprise other elements (metals and nonmetals) as impurities, e.g. as a result of the catalytically active components used containing impurities or as a result of constituents of the components used in the process of the present invention being incorporated into the platinum metal coating during the process for producing the catalysts of the present invention, for example alkali and alkaline earth metals, phosphorus, boron and halogens.

The aqueous medium used in step c) preferably further comprises at least one compound of a metal of transition group 6, 7 or 1 or the iron group or of bismuth.

The additive components may be present in amounts of from 0.001 to 25% by weight, based on the platinum metal content. Additive components used as promoters or dopants are generally present in amounts of from 0.01 to 20% by weight, preferably from 0.1 to 15% by weight and in particular from 0.5 to 10% by weight, based on the platinum metal content.

In the process of the present invention, the platinum metals are preferably used as platinum metal complexes. Preference is given to using platinum metal complexes in which the platinum metal is present in the oxidation states +1 to +4. Complexes having a coordination number of four are preferred.

The process of the present invention is preferably used for producing platinum metal catalysts in which palladium is the main platinum metal component.

To produce catalysts comprising palladium and in particular catalysts comprising palladium as main platinum metal component, preference is given to palladium(II) complexes. Palladium(II) complexes in which palladium has a coordination number of 4 are particularly useful.

Preference is given to combinations of platinum metal ions and ligand whose complex formation constant is >1000 and in particular >10000.

Suitable combinations of ligands and counterions for palladium complexes and for platinum metal complexes other than those of palladium can be selected on the basis of charge neutrality.

Suitable negatively charged ligands are, for example, selected from among halides and pseudohalides, e.g. chloride, bromide, iodide, CN, OCN and SCN, $C_1$–$C_6$-carboxylic acids such as formic acid, acetic acid and propionic acid and their salts, chelating ligands, e.g. ethylenediaminetetraacetic acid (EDTA), nitrilotriacetic acid, 1,2-diaminocyclohexanetetraacetic acid and their salts, aminophosphonic acids such as nitromethylenephosphonic acid, diketonates such as acetylacetonate, hydroxycarboxylic acids such as glycolic acid, lactic acid, tartaric acid and gluconic acid, and their salts. Suitable electrically neutral ligands are, for example, alkyl nitriles such as acetonitrile, amines such as ammonia, primary, secondary and tertiary $C_1$–$C_6$-alkylamines such as ethylamine, n-propylamine, isopropylamine, n-butylamine, tert-butylamine, hexylamine, dimethylamine, diethylamine, diisopropylamine, di-n-butylamine, trimethylamine, triethylamine, tripropylamine, N,N-dimethylethylamine, N,N-dimethylisopropylamine and N,N-dimethylbutylamine, diamines, triamines, tetramines and polyamines, e.g. ethylenediamine, diethylenetriamine and triethylenetetramine, nonaromatic and aromatic cyclic amines such as pyrrolidine, piperidine, morpholine, piperazine, pyrrole and their n-$C_1$–$C_6$-alkyl derivatives, pyridine and phenanthroline, phosphines such as tertiary $C_1$–$C_6$-alkylphosphines and $C_6$–$C_{12}$-arylphosphines, in particular triphenylphosphine, and also sulfides such as $C_1$–$C_6$-monoalkyl and -dialkyl sulfides, $C_6$–$C_{12}$-monoaryl and -diaryl sulfides and oxygen compounds, di-$C_1$–$C_6$-alkanols and phenols and also their ethers.

Particularly preferred complexing ligands are the halides chloride and bromide; amines, in particular ammonia and triethylamine, cyanide and ethylenediaminetetraacetic acid and its di-, tri- or tetra-alkali metal (e.g. sodium) salts or ammonium salts. Preferred counterions are alkali metals such as lithium, sodium and potassium, alkaline earth metals such as magnesium and calcium, nitrite, nitrate and ammonium.

Suitable platinum metal complexes are preferably soluble in water to an extent of at least 0.01% by weight at room temperature (25° C.). According to the present invention, the platinum metal complex(es) is/are used in an aqueous medium in such a concentration that the platinum metal content of the solution is in the range from 0.001 to 2 g/l, preferably in the range from 0.1 to 0.5 g/l.

Preferred palladium complexes are $H_2PdHal_4$, $M_2PdHal_4$, $M_2Pd(CN)_4$, $(NH_4)_2PdHal_4$, $Pd(NH_3)_4Hal_2$, $Pd(NH_3)_4(NO_3)_2$ and $Pd(NH_3)_4(CN)_2$, where M is an alkali metal, in particular sodium or potassium, and Hal is a halogen atom, in particular chlorine, bromine or iodine.

Further preferred platinum metal complexes are $(NH_4)_2IrCl_6$, $H_2PtCl_4$, $(NH_4)_2PtCl_4$, $Na_2PtCl_4$ and $K_2PtCl_4$.

The aqueous medium further comprises at least one reducing agent in completely or partly dissolved form. Suitable reducing agents for steps b) and c) are all substances or mixtures whose redox potential is below the redox potential of the platinum metal complex used. Preference is given to substances having a standard potential in aqueous medium of less than +0.5 volt, more preferably less than 0 volt. The reducing agent or reducing agent mixture is soluble in the aqueous medium to an extent of at least 1% by weight, preferably at least 10% by weight, at room temperature (25° C.). In preferred embodiments of the present invention, the reducing agent or the reducing agent mixture is virtually completely soluble in the aqueous medium.

Examples of suitable reducing agents are carboxylic acids such as formic acid, citric acid, lactic acid, tartaric acid and in particular the salts of carboxylic acids, preferably the alkali metal, alkaline earth metal, ammonium and $C_1$–$C_{10}$-alkylammonium salts, phosphorus or hypophosphorus acid, the salts of phosphorus or hypophosphorus acid, in particular the alkali metal or alkaline earth metal salts, $C_1$–$C_{10}$-alkanols such as methanol, ethanol and isopropanol, sugars such as aldoses and ketoses in the form of monosaccharides, disaccharides and oligosaccharides, in particular glucose, fructose and lactose, aldehydes such as formaldehyde, boron-hydrogen compounds such as boron hydrides, boranes, metal boranates and borane complexes, e.g. diborane, sodium borohydride and aminoboranes, in particular trimethylaminoborane, hydrazine and alkylhydrazines such as methylhydrazine, hydrogendithionites and dithionites, in particular sodium and potassium hydrogendithionites, sodium, potassium and zinc dithionites, hydrogensulfites and sulfites, in particular sodium and potassium hydrogensulfites, sodium, potassium and calcium sulfites, hydroxylamine and urea, and also mixtures thereof.

Preferred reducing agents for step c) are sodium and potassium hypophosphites, ammonium formate, trimethylamine-borane, sodium borohydride, sodium dithionite and sodium hydrogendithionite, and also mixtures of ammonium formate and sodium hypophosphite.

In general, use is made of at least one redox equivalent, based on the sum of the platinum metals and additive components (e.g. promoters/dopants), of reducing agent. The reducing agent is preferably used in excess. Preference is given to a molar ratio of reducing agent to platinum metal of from 10:1 to 100:1, particularly preferably from 20:1 to 60:1, for example about 30:1, about 40:1 or about 50:1.

In step c), an aqueous medium having a pH of greater than 6 is preferably used for the electroless deposition of the platinum metal. The pH is preferably in a range from 7 to 14, in particular from 8 to 12. For this purpose, it may be necessary to add at least one base to the aqueous medium comprising the platinum metal complex and the reducing agent in order to obtain the desired pH. For the purposes of the present invention, bases are all substances or compounds which are able to adjust the pH of the aqueous medium to the desired value. In particular, use is made of bases which have complex-stabilizing properties, i.e. have at least partial Lewis base character. The base is preferably selected from among metal oxides, metal hydroxides, in particular alkali metal hydroxides such as sodium hydroxide and potassium hydroxide, metal carbonates, in particular alkali metal and alkaline earth metal carbonates, e.g. lithium carbonate, sodium carbonate, potassium carbonate, magnesium carbonate and calcium carbonate, nitrogen bases, in particular ammonia, primary, secondary and tertiary amines as have been described above for the nitrogen-containing complexing ligands. Buffer systems, in particular those comprising the abovementioned bases, salts of the abovementioned bases and/or suitable acids, are likewise suitable. Particularly preferred bases are ammonia and sodium hydroxide.

For the purposes of the present invention, aqueous media are substances or mixtures which are liquid under the process conditions and contain at least 10% by weight, preferably at least 30% by weight and in particular at least 50% by weight, of water. The part other than water is preferably selected from among inorganic or organic substances which are at least partially soluble in water or at least partially miscible with water. For example, the substances other than water are selected from among organic solvents, $C_1$–$C_{22}$-alkanols, in particular methanol, ethanol, n-propanol, isopropanol, n-butanol, sec-butanol, tert-butanol, pentanoles and hexanoles, $C_4$–$C_8$-cycloalkyl ethers such as tetrahydrofurans, pyrans, dioxanes and trioxanes, $C_1$–$C_{12}$-dialkyl ethers such as dimethyl ether, dibutyl ether and methyl butyl ether, and customary auxiliaries as are used in processes for electroless deposition.

The aqueous medium preferably contains less than 40%, in particular less than 30% and particularly preferably less than 20%, of organic solvent.

In preferred embodiments of the process of the present invention, the aqueous medium is essentially free of organic solvents.

Apart from at least one compound or complex of a platinum metal and the reducing agent, the aqueous solution preferably further comprises at least one ligand (complexing agent). The ligand preferably contains a halogen, nitrogen, and/or phosphorus atom. Complexing agents for the purposes of the present invention are ions or compounds which are able to stabilize metal ions in aqueous media. In general, such complexing agents are donors or salts of donors. Suitable donors generally have a free electron pair which can interact with the metal ions. Complexing agents which have the abovementioned heteroatoms as donors are particularly suitable for the process of the present invention. Examples of suitable complexing agents are the metal salts, in particular the alkali metal and alkaline earth metal salts, of the compounds mentioned above as complexing ligands for the platinum metals.

Particularly useful complexing agents are hydrohalic acids such as hydrogen bromide, hydrogen chloride and hydrogen iodide, the metal salts of the abovementioned hydrohalic acids, in particular the alkali metal and alkaline earth metal salts, and also tin dihalides, zinc dihalides, ammonium salts such as ammonium chloride, ammonium bromide, ammonium iodide, ammonium nitrite, ammonium nitrate, the alkali metal, alkaline earth metal and ammonium salts of carboxylic acids and hydroxycarboxylic acids, e.g. sodium tartrate and/or potassium tartrate.

In general, platinum metal complex, reducing agent, any base used and any complexing agent used can be added in any order to the aqueous medium. Preference is given to adding at least part of the base to the aqueous medium before adding the reducing agent.

In one embodiment of the process of the present invention, step c) is carried out by firstly introducing the platinum metal complex and any complexing agent and/or base used into the aqueous medium and subsequently adding the reducing agent.

The temperature in step c) is generally in a range from 0 to 100° C., preferably from 30 to 100° C. and in particular from 40 to 85° C.

The active component, i.e. the platinum metal or platinum metals and any additive components present generally make up from $5 \times 10^{-4}$ to 5% by weight, in particular from $10^{-3}$ to 1% by weight, particularly preferably from 0.01 to 1.0% by weight, of the total ass of the catalyst (support+ catalytically active coating).

If an additional complexing agent is added to the solution, it is generally used in an amount of from 0.1 to 10000 equivalents, preferably from 1 to 1000 equivalents, particularly preferably from 10 to 600 equivalents, based on the platinum metal component.

For example, the activated nonmetallic support is, in step c), firstly brought into contact with the aqueous medium if the aqueous medium comprises at least the platinum metal complex, the reducing agent, at least part of the base and, if desired, the additional complexing agent. Likewise, the support can firstly be brought into contact with all the abovementioned components apart from the platinum metal. The platinum metal is then added at the reaction temperature or a temperature which is, for example, up to 30° C. lower. For the purposes of the present invention, "reaction temperature" is the temperature at which the deposition of the platinum metal of the support occurs.

In the process of the present invention, it has been found to be advantageous to ensure sufficient circulation of the reaction solution or the reaction mixture during deposition of the platinum metal on the support in step c), e.g. by pumping or stirring.

The reaction time required to deposit the platinum metal on the supports is generally from 0.5 to 500 minutes, preferably from 1 to 300 minutes and particularly preferably from 2 to 60 minutes.

In the process of the present invention, more than 70% by weight, preferably more than 80% by weight and particularly preferably more than 90% by weight, of the platinum metals used are preferably deposited on the support. The platinum metal is generally bound so strongly to the metallic support that it is not appreciably detached as a result of contact with liquids and gases when used in catalytic reactions.

Additive components, in particular the elements suitable as promoters or dopants, can, if desired, be introduced together with the platinum metal into the aqueous medium, so that the deposition of the platinum metal and the incorporation of the additive components occur essentially simultaneously. The addition of the additive components to the reaction solution can also be carried out toward the end or after the end of the deposition of platinum metal, as a result of which the additive components are incorporated preferentially at the surface of the active components. The additive components can also be applied to the catalysts of the present invention in a separate second step, e.g. by deposition from the vapor phase or by electroless deposition from aqueous or nonaqueous media. The application of additive components to the catalysts of the present invention in a separate second step is particularly advantageous when application of the additive components specifically to the surface of the active component is desired. Furthermore, deposition conditions different from the conditions employed according to the present invention can be selected for the second step.

Step d)

The catalysts obtained in step c) can subsequently be activated at from 0 to 500° C., preferably from 10 to 350° C., and pressures in the range from atmospheric pressure to 200 bar gauge pressure. The activation can, for example, be carried out in the presence of water and/or hydrogen. These can be used in the form of mixtures with an inert gas such as nitrogen. Preference is given to activation using hydrogen. The temperature is preferably from 10 to 200° C., in particular from 30 to 150° C. The pressure is preferably from 1 to 150 bar, in particular from 10 to 100 bar and particularly preferably from 30 to 70 bar. Activation is generally carried out for from 0.1 to 10 hours, preferably from 1 to 5 hours. In a preferred embodiment of the process of the present invention, the activation of the catalysts is carried out in the presence of the aqueous reaction medium which is described below for the synthesis according to the present invention of hydrogen peroxide.

In a preferred embodiment of the process of the present invention, the catalysts of the present invention are produced by dissolving at least 0.01 to 3 g/l, preferably from 0.05 to 0.3 g/l, of at least one platinum metal complex (weights based on the metal), if desired from 0.0001 to 0.3 g/l, preferably from 0.001 to 0.03 g/l, of at least one further element compound and, based on the platinum metal, at least 20, preferably 50 and particularly preferably at least 100, equivalents of a complexing agent and from at least 10 to 100, preferably from 20 to 80 and particularly preferably from 40 to 60, equivalents of a reducing agent in an aqueous medium.

The present invention further provides a catalyst obtainable by a process as described above.

The invention also provides platinum metal catalysts comprising a nonporous nonmetallic support and a catalytically active coating applied thereto, wherein the catalytically active coating comprises discrete platinum metal particles having a mean particle diameter of less than about 1 μm, preferably less than about 100 nm, immobilized on the support surface. The platinum metal particles preferably have a mean diameter of more than about 1 nm and can, for example, have diameters in the range from about 20 to 100 nm. The discrete particles preferably have an approximately spherical shape.

Particular preference is given to a catalyst in which the nonporous nonmetallic support consists essentially of glass ceramic or a polymer.

Such catalysts preferably have a platinum metal content in the range from 0.01 to 50 g/kg of support. The catalysts obtainable by this process display a selectivity in the direct synthesis of hydrogen peroxide from the elements of greater than 60%, in particular greater than 70% and particularly preferably greater than 80%.

The catalysts of the present invention are preferably used for the hydrogenation of organic and inorganic compounds, in particular for the hydrogenation of organic compounds such as olefins, e.g. ethylene, propylene, acetylene or butadiene, carbonyl compounds, e.g. aldehydes or ketones, and aromatics, e.g. benzene, particularly preferably for the hydrogenation of oxygen.

The present invention further provides a process for preparing hydrogen peroxide, which comprises bringing a catalyst as described above in a liquid medium, preferably in essentially aqueous solution into contact with an oxygen/hydrogen mixture having a mixing ratio in the range from approximately 5:1 to 100:1, in particular 5:1 to 30:1.

The present invention likewise provides for the use of the catalysts of the present invention for the synthesis of hydrogen peroxide from the elements, both by the anthraquinone process or an analogous process and by direct synthesis, i.e. direct reaction of oxygen and hydrogen over a platinum metal catalyst in a liquid medium. Suitable processes are described, for example, in WO 98/16463, which is hereby fully incorporated by reference. The use of the catalysts of the present invention for the direct synthesis of $H_2O_2$ is particularly preferred.

Suitable reactors for the synthesis of $H_2O_2$ are described, for example, in EP-A-068 862, EP-A-201 614 and EP-A-448 884. Particular preference is given to tube reactors in which the catalyst of the present invention is present as a bed or is fitted in the form of cylindrical catalyst units. Optimum flow conditions for gas and liquid can be ensured by appropriate shaping of the supports, as described above.

In a preferred embodiment, the reaction is carried out with liquid and gas flowing in cocurrent in a flooded reactor. The liquid phase preferably trickles from the top downward over the catalyst bed. Here, the gas can be passed through the reactor in cocurrent or in countercurrent, preferably in cocurrent.

The hydrogen is preferably fed into the reactor via one or more intermediate feed points downstream of the feed point for the oxygen or the air. The empty tube velocity of reaction gas and reaction medium is preferably in a range from about 20 to 7000 m/h, particularly preferably in a range from 50 to 1400 m/h.

As reaction medium, preference is given to using water and/or $C_1$–$C_3$-alkanols, in particular water and/or methanol. When water is used as reaction medium, upto 20% by weight of the alcohol, preferably methanol, can be added to it. If an alcoholic reaction medium is used, it can contain upto 40% by weight, preferably upto 20% by weight and particularly preferably upto 5% by weight, of water. Very particular preference is given to using water as sole reaction medium. To stabilize the hydrogen peroxide against decomposition, acids whose pKa is preferably less than that of acetic acid, in particular mineral acids such as sulfuric acid, phosphoric acid or hydrochloric acid, are added to the reaction medium. The acid concentration is generally at least $10^{-4}$ mol/liter, preferably from $10^{-3}$ to $10^{-1}$ mol/liter. Furthermore, traces of bromide or chloride are generally also added in concentrations of from 1 to 1000 ppm, preferably from 5 to 700 ppm and particularly preferably from 50 to 600 ppm. However, it is also possible to use other stabilizers such as formaldehyde.

The reaction gas, which may comprise not only hydrogen and oxygen but also inert gases such as nitrogen or noble gases, generally has an $O_2$:$H_2$ ratio in the range from 2:1 to 1000:1. Preference is given to using a molar ratio in the range from 5:1 to 100:1, in particular from 20:1 to 100:1. The oxygen used in the reaction gas can also be mixed in the form of air into the reaction gas.

In a preferred embodiment, the reaction gas is circulated. In this case, the molar ratio in the fresh gas mixture is in the vicinity of stoichiometry, preferably in the range from 1.5:1 to 0.5:1. The molar ratio of $O_2$:$H_2$ in the circulating gas should be in the range from 5:1 to 1000:1, preferably in the range from 20:1 to 100:1. The reaction can be carried out at atmospheric pressure or at gauge pressures upto 200 bar. The pressure is preferably from 10 to 300 bar, in particular from 10 to 80 bar. The reaction temperature can be in a range from 0 to 80° C., preferably from 5 to 60° C. and in particular from 25 to 55° C. The partial pressures of the reaction gases in the reaction gas mixture both in the reactor and in the circulating gas are preferably selected so that the hydrogen concentration is below the lower explosion limit under the reaction conditions.

The process described makes it possible to prepare hydrogen peroxide solutions having hydrogen peroxide contents above 2% by weight, preferably in the range from 3 to 25% by weight. The concentration can be preselected by setting the streams in the desired manner. The selectivity of hydrogen peroxide formation is, for example, above 65%, preferably $\geq 70\%$. Long-term tests have shown that no decrease, or only a slight decrease, in the catalyst activity and selectivity can be observed even after an operating time of more than 40 days.

The invention further provides a process for catalytic reduction by reacting an inorganic or organic compound containing at least one hydrogen acceptor group with hydrogen in the presence of at least one catalyst according to the present invention, as described above.

The catalysts of the present invention are advantageous for the hydrogenation of carbon-carbon double and triple bonds.

The invention is illustrated by the nonrestrictive examples below.

EXAMPLES

I. Catalyst Production

Catalyst 1

850 ml of soda-lime glass spheres having a diameter of 1 mm are mixed with 850 ml of silicon carbide abrasive powder in a rotating flask for 24 hours. The spheres are poured onto a suction filter with perforated plate and the abrasive is washed out with water. The roughened glass spheres are subsequently placed on a G3 frit. The glass spheres thus treated had a pore volume below the determination limit of Hg porosymmetry and a BET surface area of 0.024 $m^2/g$. A solution of 10 g of tin(II) chloride and 20 ml of concentrated hydrochloric acid in 2 l of water is made up and is allowed to seep through the glass spheres over a period of 2 minutes. The spheres on the frit are then washed with 2 l of water. A solution of 0.4 g of palladium chloride and 2 ml of concentrated hydrochloric acid in 2 l of water is subsequently allowed to seep through the layer of glass spheres, again over a period of 2 minutes, and the spheres are again washed with water. The entire procedure is repeated another five times. The activated spheres are then dried overnight at 75° C. and 100 mbar.

One third of the activated glass spheres are placed in a double-walled glass tube having a length of 1 m and a diameter of 2.2 cm. The glass tube is connected to a peristaltic pump for circulating the liquid and a thermostatted bath for heating via the double wall. A solution of 14.2 g of sodium hypophosphite, 32.8 g of ammonium chloride and 47.5 ml of 25% strength ammonia in 412 ml of water is placed in the tube, the circulating pump is switched on and the tube is heated to an internal temperature of 58° C. by means of the thermostatted bath. A solution of 265 mg of sodium tetrachloropalladate and 1 mg of hexachloroplatinic acid in 10 ml of water is subsequently added. Vigorous evolution of gas occurs and the glass spheres immediately become black. After 5 minutes, the liquid is drained off, the spheres are washed with water and dried overnight at 75° C.

and 100 mbar. Analysis shows that 87.4% of the available palladium and 77% of the platinum have been deposited on the support. The coating procedure is repeated using a further third of the activated catalyst each time. Finally, all three portions are mixed to give Catalyst 1.

Catalyst 2

Roughening and activation with tin and palladium are repeated as described for Catalyst 1 using soda-lime glass spheres having a diameter of 2 mm. The roughened glass spheres had an Hg porosymmetry pore volume of 0.005 ml/g and a BET surface area of 0.018 $m^2/g$.

270 ml of the activated glass spheres are placed in the coating tube. A solution of 32.4 g of sodium hypophosphite, 72.9 g of ammonium chloride and 108 ml of 25% strength ammonia in 540 ml of water is added and the contents of the tube are heated to 42° C. While maintaining pumped circulation. A solution of 542 mg of sodium tetrachloropalladate and 2.05 mg of hexachloroplatinic acid in 17 ml of water is subsequently added and the contents of the tube are heated to 46° C. while continuing to maintain circulation. After 5 minutes, the liquid is drained and the supported catalyst is washed with water. The catalyst is subsequently dried overnight at 75° C. and 100 mbar. The procedure is repeated twice more and the three portions are mixed to give the catalyst sample 2.

Catalyst 3

1 mm glass spheres are roughened and activated as described for Catalyst 1.

270 ml of the activated glass spheres are placed in the coating tube. A solution of 168 mg of sodium tetrachloropalladate and 0.70 mg of hexachloroplatinic acid, 80 mg of disodium tungstate, 30.6 g of ammonium chloride and 45 ml of 25% strength ammonia in 438 ml of water are added and the contents of the tube are heated to 42° C. while maintaining circulation. A solution of 13.6 g of sodium hypophosphite in 14.6 g of water is subsequently added and the contents are heated further to 46° C. After 5 minutes, the solution is drained off and the spheres are washed with water. Subsequent analysis shows that 88% of the palladium and 39% of the platinum have been deposited. The procedure is repeated in the same way using the other one third portions of the activated support, and the three parts are subsequently combined to give Catalyst 3. Analysis indicated a palladium content of 180 mg/kg.

Catalyst 4

The procedure described for producing Catalyst 1 is repeated without the hexachloroplatinic acid. Analysis indicated a palladium content of 115 mg/kg.

Catalyst 5

The procedure described for producing Catalyst 3 is repeated with omission of the roughening step. Analysis indicated a palladium content of 210 mg/kg.

Catalyst 6

The procedure described for producing Catalyst 3 is repeated, but the surface was roughened not mechanically but by etching with hydrofluoric acid.

Catalyst 7

220 ml of glass spheres having a diameter of 1 mm are roughened and activated as described for Catalyst 1. The support is subsequently treated in the coating tube with a solution of 187.2 mg of ruthenium chloride and 10 ml of 25% strength ammonia in 200 ml of water and heated to 27° C. while maintaining circulation. A solution of 200 mg of sodium borohydride in 10 ml of water is added in two portions. After 20 minutes, the contents of the tube are heated to 40° C. and the reaction solution is circulated for a further 15 minutes at this temperature. After draining off the liquid, the catalyst is washed with water and dried at 75° C. and 100 mbar.

Analysis shows that 87% of the available ruthenium have been deposited on the support.

Catalyst 8

Comparative Example Using a Porous Support 375 ml of α-aluminum oxide spheres having a diameter of from 1 to 1.5 mm are activated with tin and palladium as described for Catalyst 1. They are subsequently placed in the tube reactor and treated with a solution of 41.9 g of ammonium chloride, 18.6 g of sodium hypophosphite and 62 ml of 25% strength ammonia in 600 ml of water and heated to 60° C. A solution of 346 mg of sodium tetrachloropalladate and 1.5 mg of hexachloroplatinic acid in 13 ml of water is added and the contents of the tube are heated to 40° C. After 10 minutes, the liquid is drained off and the catalyst is washed with water.

The procedure is repeated once more and the two parts are combined to give Catalyst 8.

Catalyst 9

700 ml of spheres made of granulated steatite (having an Hg porosymmetry pore volume of 0.011 ml/g and a BET surface area of 0.031 $m^2/g$) and having a diameter of 2–3 mm are treated twice with palladium chloride and tin chloride as described for Catalyst 1. 340 ml of the activated spheres are placed in the coating reactor. After addition of a solution of 18.6 g of sodium hypophosphite, 41.9 g of ammonium chloride and 62 ml of 25% strength ammonia in 500 ml of water, the contents of the reactor are heated to 29° C. while maintaining pumped circulation. A solution of 83.4 mg of sodium tetrachloropalladate and 4.8 mg of hexachloroplatinic acid in 8 ml of water is subsequently added and the mixture is circulated further. After 15 minutes, the liquid is drained off, the catalyst is washed with water until free of salts and dried at 75° C. under reduced pressure. The procedure is repeated once more and the two portions are then mixed to give Catalyst 9. Analysis shows that 95% of the palladium and 100% of the platinum have been deposited on the support.

Catalyst 10

700 ml of steatite spheres having a diameter of 1.5–2.5 mm (having a pore volume below the detection limit of Hg porosymmetry and a BET surface area of 0.005 $m^2/g$) are treated twice with palladium chloride and tin chloride as described for Catalyst 1. 340 ml of the activated spheres are placed in the coating reactor. After addition of a solution of 18.6 g of sodium hypophosphite, 41.9 g of ammonium chloride and 62 ml of 25% strength ammonia in 500 ml of water, the contents of the reactor are heated to 44° C. while maintaining pumped circulation. A solution of 83.4 mg of sodium tetrachloropalladate and 4.8 mg of hexachloroplatinic acid in 8 ml of water is subsequently added and the mixture is circulated further. After 20 minutes, the liquid is drained off, the catalyst is washed with water until free of salts and dried at 75° C. under reduced pressure. The procedure is repeated once more, and the two portions are then mixed to give Catalyst 10.

Catalyst 11

740 ml (447 g) of polystyrene extrudates having a diameter of 1 mm and a length of 1.1 mm (having a pore volume below the detection limit of Hg porosymmetry and a BET surface area of 0.029 $m^2/g$) are activated with tin and palladium as described for Catalyst 1. Half of the support is then placed in the coating reactor, a solution of 18.6 g of sodium hypophosphite, 41.9 g of ammonium chloride and 62 ml of 25% strength ammonia in 620 ml of water is added and the contents of the reactor are heated to 42° C. A solution of 346 mg of sodium tetrachloropalladate and 1.43 mg of hexachloroplatinic acid in 10 ml of water is subsequently added while maintaining pumped circulation. After 10 minutes, the solution is drained off and the extrudates are washed with water. The second half of the activated support is treated with the same chemicals as described above in a stirred flask, with the mixture being stirred at 1000 rpm at 45° C. The catalyst is filtered off and washed with water. The two parts are mixed and dried at 50° C. and 100 mbar. Analysis shows that the noble metals have been deposited quantitatively. Analysis indicates a palladium content of 285 mg/kg.

Catalyst 12

840 ml of 3 mm pellets of a polyamide 6 (Ultramid® B3 from BASF AG) (having a pore volume below the detection limit of Hg porosymmetry and a BET surface area of 0.027 $m^2/g$) are activated with tin and palladium as described for Catalyst 1. 240 ml of the pellets are placed in the coating tube, a solution of 9.6 g of sodium hypophosphite, 21.6 g of ammonium chloride and 32 ml of 25% strength ammonia in 160 ml of water is added and the contents of the tube are heated to 45° C. Subsequently, while maintaining pumped circulation, a solution of 137 mg of sodium tetrachloropalladate and 0.52 mg of hexachloroplatinic acid in 10 ml of water is added followed by 67.7 mg of disodium tungstate in 5 ml of water. After 25 minutes, the solution is drained off and the pellets are washed with water. The coating procedure is repeated using the remaining activated support (in 2 portions). Finally, all three portions are mixed to give Catalyst 12.

Catalyst 13

750 ml of 3 mm glass Raschig rings (having an Hg porosymmetry pore volume of 0.036 ml/g and a BET surface area of 0.034 $m^2/g$) are activated with tin and palladium as described for Catalyst 1. One third of the activated Raschig rings are placed in a double-walled glass tube having a length of 1 m and a diameter of 2 cm. The glass tube is connected to a peristaltic pump for circulating liquid and a thermostatted bath for heating via the double wall. A solution of 15.6 g of sodium hypophosphite, 35.1 g of ammonium chloride and 52 ml of 25% strength ammonia in 430 ml of water is introduced into the tube, the circulating pump is switched on and the tube is heated to an internal temperature of 46° C. by means of the thermostatted bath. A solution of 250 mg of sodium tetrachloropalladate and 1.1 mg of hexachloroplatinic acid in 10 ml of water is subsequently added. Vigorous evolution of gas occurs and the glass rings immediately become black. After 5 minutes, the liquid is drained off, the rings are washed with water and dried overnight at 75° C. and 100 mbar. The coating procedure is repeated using a further third of the activated support each time. Finally, all three portions are mixed to give Catalyst 13. Analysis indicates a palladium content of 155 mg/kg.

Catalyst 14

5 mm of soda-lime glass spheres are roughened and activated as described for Catalyst 1. 115 ml of the activated glass spheres are placed in the coating tube. A solution of 6.8 g of sodium hypophosphite, 15.3 g of ammonium chloride and 23 ml of 25% strength ammonia in 228 ml of water is added and the contents of the tube are maintained at 25° C. while maintaining pumped circulation. A solution of 38.8 mg of sodium tetrachloropalladate in 3.8 ml of water is subsequently added and pumped circulation is continued. After 12 minutes, the liquid is drained off and the supported catalyst is washed with water. The catalyst is subsequently dried overnight at 75° C. and 100 mbar. The coating procedure is repeated using another 115 ml of the activated class spheres, and the two portions are mixed to give Catalyst 14. The palladium content of the catalyst is 71 mg/kg.

Catalyst 15

100 ml of steatite spheres having a diameter of 1.5–2.5 mm are treated twice with palladium chloride and tin chloride as described for Catalyst 1. The activated spheres are placed in the coating reactor. After addition of a solution of 40 mg of hexachloroplatinic acid (as 1% strength solution in water), 21.6 g of ammonium chloride and 32 ml of 25% strength ammonia in 220 ml of water, the contents of the reactor are maintained at 24° C. while maintaining pumped circulation. A solution of 200 mg of sodium borohydride in 7 ml of water is subsequently added in two portions and the mixture is circulated further. After 40 minutes, the liquid is drained off, the catalyst is washed with water until free of salts and dried at 75° C. under reduced pressure. Analysis shows that 60% of the platinum have been deposited on the support.

II. Use Properties

The properties of the catalysts were tested in the direct synthesis of hydrogen peroxide from hydrogen and oxygen (Examples E1 to E19) and in the hydrogenation of 2-ethylanthraquinone and hydrodehydrolinalool (Examples E20 and E21).

Examples E1–E9 and E11–E19, Comparative Example CE10

Example 1

A double-walled reactor having an internal diameter of 2.1 cm and a length of 2 m is charged with Catalyst 1. At 40° C. and a pressure of 50 bar, a solution of 5 g/l of phosphoric acid and 120 mg/l of hydrogen bromide in water is allowed to trickle through the catalyst bed at a rate of 250 ml per hour. At the same time, a mixture of 3% of hydrogen and 97% of oxygen is circulated by means of a gas compressor through the catalyst bed from the top downward at a rate of 10400 Standard 1/h. The gas mixture is generated by means of two mass flow meters for hydrogen and oxygen. Its composition is determined and adjusted with the aid of a thermal conductivity detector over which a small substream is passed as off-gas stream.

The amount of hydrogen consumed by the reaction to hydrogen peroxide and water is calculated from the mass inflows of the gases and from the off-gas stream.

The product mixture leaving the reaction tube is separated from the gases in a separator while still under pressure and is discharged from the plant in liquid form. The mass flow is balanced against the feed stream. The hydrogen peroxide content in the liquid product is determined by titration.

The selectivity based on hydrogen is calculated from the mass of the output stream, the hydrogen peroxide content and the amount of hydrogen consumed. The space-time yield is given by the amount of hydrogen peroxide formed per unit time divided by the volume of 690 ml of catalyst bed in the tube reactor.

Examples 1 to 9 and 11 to 19 and Comparative Example 10 were carried out using a method analogous to Example 1. The reaction conditions and results of the reaction are summarized in Table 1.

TABLE 1

| No. | Catalyst No. | Liquid flow (ml/h) | Gas flow (Standard 1/h) | T (° C.) | Selectivity (%) | Space-time yield (g/l × h) | $H_2O_2$ concentration (%) |
|---|---|---|---|---|---|---|---|
| E1 | 1 | 250 | 10400 | 40 | 61 | 58 | 13.1 |
| E2 | 1 | 250 | 15600 | 40 | 65 | 63 | 13.9 |
| E3 | 1 | 500 | 15600 | 41 | 71 | 77 | 9.4 |
| E4 | 1 | 500 | 10400 | 49 | 64 | 95 | 11 |
| E5 | 2 | 500 | 10400 | 38 | 83 | 61 | 7.5 |
| E6 | 2 | 250 | 10400 | 40 | 69 | 55 | 12.5 |
| E7 | 2 | 150 | 10400 | 40 | 65 | 48 | 16.9 |
| E8 | 3 | 500 | 10400 | 40 | 59 | 61 | 7.4 |
| E9 | 3 | 500 | 10400 | 50 | 52 | 88 | 10.1 |
| CE10 | 8 | 500 | 10400 | 40 | 58 | 8 | 0.9 |
| E11 | 10 | 1000 | 10400 | 50 | 84 | 91 | 5.3 |
| E12 | 10 | 1000 | 10400 | 55 | 79 | 103 | 5.9 |
| E13 | 10 | 500 | 10400 | 55 | 72 | 96 | 10.2 |
| E14 | 11 | 250 | 10400 | 29 | 25 | 25 | 5.6 |
| E15 | 13 | 250 | 15600 | 40 | 65 | 34 | 8.2 |
| E16 | 13 | 500 | 15600 | 40 | 75 | 37 | 4.7 |
| E17 | 13 | 250 | 15600 | 50 | 60 | 44 | 10.4 |
| E18 | 13 | 500 | 10400 | 50 | 79 | 33 | 4.2 |
| E19 | 9 | 500 | 10400 | 40 | 90 | 43 | 5.5 |

As Comparative Example 10 using the catalyst 8 which is not according to the present invention demonstrates, catalysts on a porous support as described in the prior art have a significantly lower activity than the catalysts of the present invention.

Example 20

Hydrogenation of 2-ethylanthraquinone

A double-walled reactor having an internal diameter of 2.1 cm and a length of 2 m is charged with Catalyst 4. At 40° C. and a hydrogen pressure of 10 bar, a solution of 13% by weight of 2-ethylanthraquinone in a mixture of 70% by weight of a hydrocarbon mixture (Shellsol®) and 30% by weight of tetrabutylurea is allowed to trickle continuously through the catalyst bed at a rate of 2700 ml/h.

The hydrogenated solution leaving the reaction tube is separated from the gas in a separator and discharged from the plant in liquid form.

Analysis of the output solution by gas chromatography indicated a conversion of 73% and a selectivity of 99.9% in respect of 2-ethylanthrahydroquinone.

Example 21

Hydrogenation of Hydrodehydrolinalool

Catalyst 14 (152 ml) together with hydrodehydrolinalool is placed in a double-walled tube having a diameter of 2 cm. By means of appropriate pumps, the liquid and hydrogen are circulated at 1.1 bar and 80° C. at cross-sectional throughputs of 200 $m^3/m^2$ in each case. The acetylenic alcohol is hydrogenated to hydrolinalool at a conversion rate of 15%/h and a selectivity of >98%.

We claim:

1. A process for producing a catalyst comprising at least one platinum metal supported on a nonporous nonmetallic support; wherein said platinum metal is selected from the group consisting of Ru, Os, Rh, Ir, Pd, Pt, and combinations thereof, and wherein the support is in the form of a particulate structure having a particle size of from 0.25 nm to 10 mm or in the form of a shaped body, which is selected from the group consisting of a sphere, a pellet, a short extrudate, an open-walled cylinder having inwardly bent protrusions, a cylinder, a saddle, a cylindrical mesh packing element, a hackette, a spiral, a helix, a monolith comprising woven fabric, said process comprising:

activating the support and electrolessly depositing said at least one platinum metal on the activated support by contacting the support with an aqueous medium comprising at least one compound or one complex of said platinum metal and at least one reducing agent.

2. A process as claimed in claim 1, wherein said activating comprises contacting the support with a reducing agent and a salt of a platinum metal.

3. A process as claimed in claim 1, which further comprises roughening the support prior to said activating the support.

4. A process as claimed in claim 1, wherein the support has a mercury porosymmetry pore volume of not more than 0.1 ml/g.

5. A process as claimed in claim 1, wherein the aqueous medium further comprises at least one compound of a metal of transition group 6, 7 or 1 or the iron group or of bismuth.

6. A process as claimed in claim 1, wherein the aqueous medium further comprises at least one ligand which is capable of forming a complex with the at least one platinum metal.

7. A process as claimed in claim 1, wherein a reducing agent having a standard potential of not more than +0.5V is used for the electroless deposition.

8. A process as claimed in claim 1, wherein the second aqueous medium comprising the at least one reducing agent is selected from the group consisting of tin(II) chloride and titanium(III) chloride.

9. A process, which comprises:

hydrogenating an inorganic compound, an organic compound, or both an inorganic compound and an organic compound in the presence of the catalyst prepared by the process as claimed in claim 1.

10. A process, which comprises:

hydrogenating an organic compound having a carbon-carbon double or triple bond, in the presence of the catalyst prepared by the process as claimed in claim 1.

11. A process for preparing hydrogen peroxide by direct synthesis, which comprises contacting the catalyst prepared by the process as claimed in claim 1 in a liquid medium with oxygen and hydrogen.

12. A process for catalytic reduction, which comprises: reacting an inorganic or organic compound comprising at least one hydrogen acceptor group with hydrogen in the presence of at least one catalyst prepared by the process as claimed in claim 1.

13. A process for preparing hydrogen peroxide by direct synthesis, which comprises contacting a catalyst prepared by the process as claimed in claim 2 in a liquid medium with oxygen and hydrogen.

14. A process for producing a catalyst comprising at least one metal supported on a nonporous nonmetallic support;

wherein said metal is selected from the group consisting of Ru, Os, Rh, Ir, Pt, and combinations thereof, and wherein the support is in the form of a particulate structure having a particle size of from 0.25 nm to 10 mm or in the form of a shaped body, which is selected from the group consisting of a sphere, a pellet, a short extrudate, an open-walled cylinder having inwardly bent protrusions, a cylinder, a saddle, a cylindrical mesh packing element, a hackette, a spiral, a helix, a monolith comprising woven fabric;

said process comprising:

activating the support by contacting the support with a first aqueous medium comprising at least one compound or one complex of a palladium metal and a second aqueous medium comprising at least one reducing agent having a redox potential less than the redox potential of the one complex of the palladium metal; and electrolessly depositing at least one metal on the activated support by contacting a third aqueous medium comprising at least one compound or one complex of the metal and at least one reducing agent having a redox potential less than the redox potential of the one complex of the metal;

wherein the metal is selected from the group consisting of Ru, Os, Rh, Ir, Pt, and combinations thereof.

15. A process as claimed in claim 14, which further comprises roughening the support prior to said activating the support.

16. A process as claimed in claim 14, wherein said activating the support comprises contacting the support with the first aqueous medium and the second aqueous medium in succession.

17. A process as claimed in claim 14, wherein the support has a mercury porosymmetry pore volume of not more than 0.1 ml/g.

18. A process as claimed in claim 14, wherein the third aqueous medium further comprises at least one compound of a metal of transition group 6, 7 or 1 or the iron group or of bismuth.

19. A process as claimed in claim 14, wherein the third aqueous medium further comprises at least one ligand which is capable of forming a complex with the at least one metal.

20. A process as claimed in claim 14, wherein a reducing agent having a standard potential of not more than +0.5V is used for the electroless deposition.

21. A process as claimed in claim 14, wherein the second aqueous medium comprising the at least one reducing agent is selected from the group consisting of tin(II) chloride and titanium(III) chloride.

22. A process, which comprises:

hydrogenating an inorganic compound, an organic compound, or both an inorganic compound and an organic compound in the presence of the catalyst prepared by the process as claimed in claim 14.

23. A process for catalytic reduction by reacting an inorganic or organic compound containing at least one hydrogen acceptor group with hydrogen in the presence of at least one catalyst prepared by the process as claimed in claim 14.

* * * * *